United States Patent [19]

Stewart

[11] E Re. 29,778

[45] Reissued Sep. 26, 1978

[54] PEDIATRIC RESPIRATOR

[75] Inventor: Jeffrey L. Stewart, Brookfield, Conn.

[73] Assignee: Bio-Med Devices, Inc., Stamford, Conn.

[21] Appl. No.: 736,991

[22] Filed: Oct. 29, 1976

Related U.S. Patent Documents

Reissue of:

[64] Patent No.: 3,949,749
Issued: Apr. 13, 1976
Appl. No.: 477,194
Filed: Jun. 7, 1974

U.S. Applications:

[63] Continuation-in-part of Ser. No. 445,758, Feb. 24, 1974, Pat. No. 3,910,270.

[51] Int. Cl.[2] ..... A61M 16/00

[52] U.S. Cl. ..... 128/145.8; 128/142.3

[58] Field of Search ..... 128/145.5–145.8, 128/142.2, 142.3, 188, 203, 202, DIG. 17, 140 R, 145 R, 28

[56] References Cited

U.S. PATENT DOCUMENTS

| | | | |
|---|---|---|---|
| 2,121,311 | 6/1938 | Anderson et al. | 128/145.8 |
| 3,366,109 | 1/1968 | McAllister | 128/145.5 |
| 3,586,021 | 6/1971 | McGuinness | 128/145.6 |
| 3,604,415 | 9/1971 | Hoenig | 128/145.8 |
| 3,754,550 | 8/1973 | Kipling | 128/145.8 |
| 3,827,433 | 8/1974 | Shannon | 128/145.5 |
| 3,840,006 | 10/1974 | Buck et al. | 128/145.8 |
| 3,842,828 | 10/1974 | Bird | 128/145.8 |

FOREIGN PATENT DOCUMENTS 1,287,564 8/1972 United Kingdom.

*Primary Examiner*—Robert W. Michell
*Assistant Examiner*—Henry J. Recla
*Attorney, Agent, or Firm*—St. Onge, Steward, Johnston, Reens & Noe

[57] ABSTRACT

A respirator is described using pneumatic elements to generate a variety of operating modes. A gas mixture is passed through a patient connection which is coupled to supply the gas through a patient port to a patient. After passing the patient port the gas is controllably exhausted to atmosphere through an exhaust port in control valve. The control valve regulates the closure of the exhaust port to provide inspiration and expiration control at the patient port. Pneumatic logic elements are combined to provide automatic inspiration and expiration support with different modes such as volume limited or pressure limited and with selection over the duration of the respective breathing phases. Various operating modes are obtained with variable restrictors selectively placed with the pneumatic logic elements.

9 Claims, 1 Drawing Figure

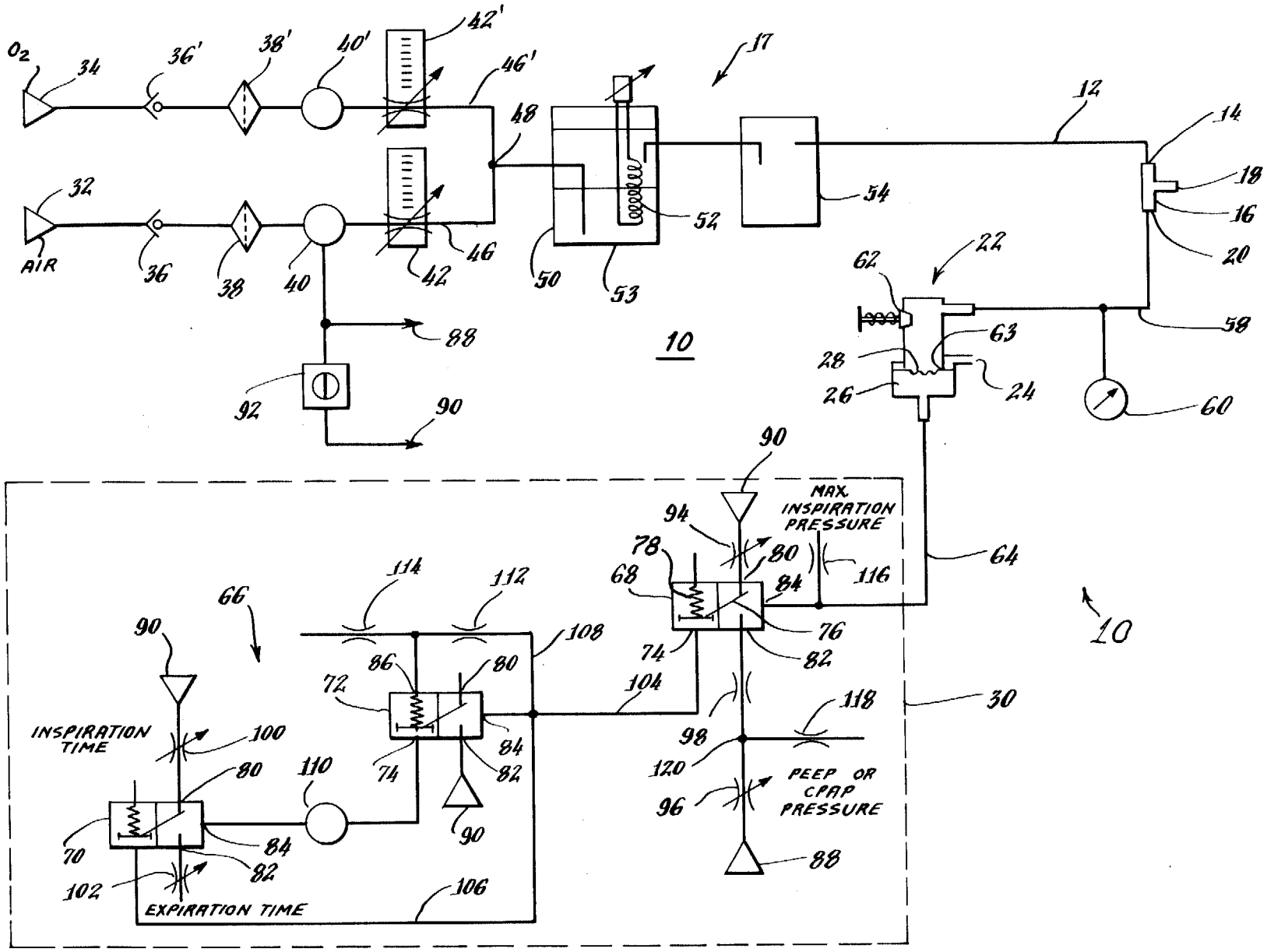
MAX. INSPIRATION PRESSURE
PEEP OR CPAP PRESSURE
INSPIRATION TIME
EXPIRATION TIME
O2
AIR

PEDIATRIC RESPIRATOR

Matter enclosed in heavy brackets [ ] appears in the original patent but forms no part of this reissue specification; matter printed in italics indicates the additions made by reissue.

This application is a continuation in part of a copending patent application entitled "Portable Volume Cycle Respirator" filed on Feb. 24, 1974 with Ser. No. 445,758, now U.S. Pat. No. 3,910,270, filed by the same inventor as this application.

This invention relates to respirators. More specifically, this invention relates to a time cycled pediatric respirator utilizing pneumatic logic elements.

BACKGROUND OF THE INVENTION

Respirators have become widely used in a large variety of applications by hospitals and medical practitioners. Respirators may be used to cure diseases such as pulmonary edema, central nervous system depressions, tetanus neonatorum, asphyxia neonatorum, respiratory distress syndromes, hyaline membrane disease as well as many others.

There are many different respirators available some of which are designed for specific diseases and others of greater complexity to provide a multitude of operational modes for different physiological requirements. For example, some respirators provide intermittent positive pressure breathing (IPPB), either with or without a positive end expiratory pressure (PEEP). Other respirators may also provide such respiratory supports known as intermittent mandatory ventilation (IMV) whereby a patient may be provided with inspirations with relatively long expirations, or continuous positive airway pressure (CPAP) to provide oxygen or other breathable gas mixtures at a constant pressure on a continuous, as needed, basis.

Respirators may involve electrical controls such as described in the U.S. Pat. to Wilson, No. 3,191,595 or a pneumatic control as described in the U.S. Pat. to Hoenig, No. 3,604,415. An intermittent positive pressure breathing respirator is described in the U.S. Pat. to Liston, No. 3,434,471.

The Hoenig patent describes a respirator using three basic pneumatic logic elements. The flow of breathable gas to the patient is not continuous but interrupted by a logic element whose opening and closure is controlled by other logic devices.

The Wilson patent describes a respirator which senses pressures generated in the gas tube leading to the patient mask to initiate control and operation of a main control valve.

Other respirators known to be available in the art provide a patient connection tube with a continuous flow of gas. The gas flow is permitted to pass through to a control valve which exhausts the gas to ambient in a controllable manner to thereby provide respiratory support at the patient mask. Such respirators utilize complex and expensive controls to generate the desired respiratory support.

SUMMARY OF THE INVENTION

In a respirator formed in accordance with the invention, a supply of breathable gas is passed to a patient through a connection having a patient port to supply the gas to the patient and a parallel coupled control port. The control port is so located that it permits the supply of breathable gas to flow continuously to an ambient environment through a control valve to thus allow the patient to draw from the gas as the patient requires. A pneumatic control circuit is coupled to the control valve to regulate the exhaust of the gas from the patient connection through the control port. The control includes pneumatic elements to provide maximum and minimum pressures at the patient port in correspondence with desired inspiratory and expiratory paressure levels. A pneumatic timing network provides timing control over inspiratory and expiratory periods.

A respirator in accordance with the invention can be formed of a conveniently portable device with a simple construction of pneumatic components. A respirator of this invention advantageously employs a few logic elements for a wide variety of respiratory support modes such as IPPB, PEEP, CPAP and IMV. A range of inspiratory to expiratory ratios are conveniently included as well as selection over operational characteristics such as volume limited mode for the delivery of fixed selectable volumes of gas or a pressure limited mode for the delivery of gas with a predetermined maximum pressure limit. The respirator provides a constant flow of breathable gas which makes the device particularly useful for pediatric applications. The respirator consumes a very small quantity of gas, thus making it particularly suitable in a portable form.

It is, therefore, an object of the invention to provide a respirator of a relatively simple, inexpensive construction yet capable of providing a large variety of respiratory support modes which can be conveniently adjusted to the physiological requirements of the patient to be treated.

BRIEF DESCRIPTION OF DRAWING

These and other objects and advantages of a respirator formed in accordance with the invention may be understood from the following description of a preferred embodiment described in conjunction with the drawing wherein The FIGURE is a schematic representation of a pneumatic respirator in accordance with the invention.

DETAILED DESCRIPTION OF EMBODIMENT

With reference to the FIGURE, a respirator 10 is shown for controlling and supplying breathable gas through a supply conduit 12 coupled to an inlet port 14 of a wye or T-shaped patient connection 16. The patient breathes gas provided by a supply 17 from a patient port 18 in the connection 16 while the gas may continue to flow through a control port 20 in the connection 16 for exhaust at a control valve 22.

Gas is continuously made available to the patient port 18 without interruption to provide respiratory support. Inspiration and expiration control are obtained by regulating the exhaust of gas passing through control port 20 to an exhaust port 24 in control valve 22. Such control is achieved by controlling the pressure of a control chamber 26 on one side of a diaphragm 28 operatively coupled to regulate the exhaust of gas from port 24. The pressure control chamber 26 in turn is regulated with a pneumatic control 30.

With the arrangement as illustrated, the patient port 18 is continuously provided with gas so that a patient's breathing demand can be met at any time without interruption.

The medicinal gas supply 17 provides air or a special mixture of oxygen, depending upon the particular requirements for the patient. A gas source 32 for air, and an oxygen source 34 are respectively connected through check-valves 36–36', filters 38–38' and pressure regulators 40–40' to flow meters 42–42'. The flow meters 42–42' are individually adjustable to provide control over the respective rate of the supply of gas. The outputs 46 of the flow meters 42 are joined to a common mixing juncture 48 coupled to pass the gas mixture through a heated humidifier 50. The heated humidifier 50 includes a suitable heater 52 and supply of water 53 and other control elements as is conventional in the art to impart the desired amount of water vapor to the medicinal gas. The humidified gas is then passed through a water trap 54 formed of a sufficiently large tank to enable water droplets to condense and settle out from the gas mixture and provide a suitable breathable medicinal gas mixture.

A conduit network formed of tubes 12, patient connection 16 and tube 58 arranges the flow of gas from the water trap 54 past the patient port 18 to control valve 22. The tubes 12 and 58 are formed of rigid small bore tubes exhibiting very low compliance. In this manner the supply of gas to the patient connection 16 is not exposed to shape changes of the tubes due to pressure variations imposed by the action of control valve 22. The tubing 12, 16 and 58 are furthermore kept small to reduce the effect of gas compression. However, the tubing is selected not too small lest the flow of gas would be unduly restricted and expiration through tube 58 would be made more difficult.

A pressure gauge 60 is coupled to tube 58 to sense and register the pressure occurring at the patient port 18. The control valve 22 includes an emergency relief valve 62 used to exhaust gas to ambient when the pressure in tube 58, and thus at the patient port 18, achieves a predetermined dangerously high level.

The passage of gas through port 24 to atmosphere and thus also the pressure at the patient connection 16, are a function of the force exerted by a diaphragm 28 on the seat 63. This force, in turn, is determined by the pressure developed in chamber 26 and area of the diaphragm 28. The pressure in chamber 26 is controlled by pneumatic network 30 coupled to chamber 26 through conduit 64.

Pneumatic logic circuit 30 is formed of a pneumatic oscillator 66 and a pressure control pneumatic bistable element 68. The pressure control bistable element 68 provides regulation for the inspiration and expiration pressures to be established at the patient connection 16 while the oscillator 66 regulates the duration of the inspiratory and expiratory periods.

The pneumatic logic control circuit 30 uses three bistable elements 68, 70 and 72 which are identical though elements 70 and 72 are coupled in oscillator arrangement. The pneumatic bistable elements are shown in schematic fashion since their physical shape may, as is well known in the art, take many different forms. Thus each element 68, 70 or 72 has a control port 74 to receive an input gas pressure with which a three port valve 76 is switched from a normal position to an actuated position as long as gas is supplied to control port 74.

Valve 76, as illustrated in the drawing, normally is biased by a spring 78 to close an input port 80 and permit the passage of gas between another input port 82 and output port 84. When gas pressure is applied to control port 74, the valve element 76 is switched against the spring bias to close input port 82 and allow gas flow between ports 80 and 84. Another control port 86 is provided to back bias spring 78. In such case the operation of spring 78 may be given a snap action effect.

Pneumatic power for network 30 is obtained from normally identical sources 88, 90 which are derived from the air regulator 40 with a shut-off valve 92 interposed between air source 90 and regulator 40. The shut-off valve 92 enables the removal of pneumatic power from most of network 30 to establish a particular mode as will be further explained.

The breathing pressure control element is provided with a variable maximum inspiratory pressure control in the form of a variable restrictor 94 which establishes the inspiration pressure through input port 80. An expiration pressure control in the form of a variable restrictor 96 is coupled through a fixed restrictor 98 to the other input port 82 of element 68.

The oscillator 66 is provided with an inspiration time control in the form of a variable restrictor 100 coupled to input port 80 of element 70. A similar restrictor for an expiration time control 102 is shown coupled to input 82 of element 70.

In the operation of the respirator 10, before gas is supplied to the bistable logic elements 68, 70 and 72, they are in the position as shown in the drawing due to the bias action of springs 78. When gas is turned on and valve 92 is open, the gas source 90 coupled to input port 82 of element 72 pressurizes line 104 connected to control port 74 of element 68, feedback line 106 coupled to control port 74 of element 70 and back bias line 108 connected to control port 86 of element 72.

Pressurization of lines 104 and 106 results in the switching of elements 68 and 70, closing their inlet ports 82 and enabling gas flow from their input ports 80 to output ports 84. In the oscillator 66, the pressurization of output port 84 of element 70 results in the delivery of gas to a volume 110 coupled between element 70 and control port 74 of element 72. The rise in pressure of volume 110 is, however, initially insufficient to overcome the combined action by spring 78 and the back bias pressure generated at control port 86 in element 72. This back bias pressure is reduced from that available in line 108 by virtue of the pair of series coupled fixed restrictors 112 and 114 bleeding gas to atmosphere.

In the bistable pressure controlling breathing element 68, gas flows through inspiration pressure control 94 to line 64 and to atmosphere through a fixed restrictor 116. The pressure in line 64 is determined by the fixed restrictor 116 and the setting of the maximum inspiratory pressure control 94. The gas pressure in line 64 pressurizes chamber 26 and thus diaphragm 28 which thereby blocks exhaust port 24 with a force proportional to the diaphragm area facing chamber 26.

The blockage of exhaust port 24 in turn prevents the escape of medicinal gas whose pressure at the patient port 18 increases. Since the compliance of the gas tubes 12 and 58 is very low relative to the compliance of the patient's respiratory system, most of the gas flows into the patient's respiratory system to initiate an inspiratory phase.

The volume of the gas supplied to the patient is a function of the flow rate of the gas as determined by the flow meters 42, 42'. The volume is further a function of the length of time that the exhaust port 24 in control valve 22 is closed as determined by the inspiration time control 100. Since the compliance of the tubing is low, and the pressure attained at the patient port 18 is primarily a function of the patient airway resistnce, the volume of gas supplied to the patient is effectively constant and the respirator operates in a volume limited mode.

The inspiratory phase continues until the pressure in volume 110 reaches a level sufficiently high to cause bistable element 72 to switch, thus blocking its inlet port 82 and opening inlet port 80. Since port 80 of element 72 is open to atmosphere, the gas in lines 104, 106 and 108 are dumped to atmosphere, allowing bistable elements 68, 70 to be reset by their respective springs 78 to their normal positions as shown in the drawing and thus begin the expiratory period.

With bistable pressure control element 68 reset, the gas in line 64 and control chamber 26 in valve 22 is allowed to flow to atmosphere through restrictor 116 and series coupled restrictors 98 and 118. The restrictor 116 is so selected that the end pressure established in line 64 is a function of the position of variable restrictor 96. Thus when the latter is set to produce gas flow at some pressure at junction 120, a residual pressure is retained in line 64 and a residual force maintained against diaphragm 28 throughout hte expiratory period.

Hence, with variable restrictor 96 set to a desired level, a positive end expiration pressure (PEEP) is obtained. Such PEEP state has been shown to be beneficial in different respiratory diseases such as hyaline membrane disease.

The expiratory period continues for a time period determined by the time needed to exhaust the gas in volume 110 through expiration time control 102 to atmosphere. When the pressure exerted by the gas in volume 110 at control port 74 of element 72 falls below the force of its spring 78, element 72 is reset to its normal position as shown in the drawing. The reset action occurs quickly with a snap action as a result of the feedback obtained along line 108.

Note that the restrictors 112, 114 are so selected that the total reset force including the force of spring 78 exerted at control port 86 of element 72 is less than the maximum setting pressure developed at control port 74 from volume 110 during the inspiratory period.

When the bistable element 72 has been reset, a new cycle commences in the manner described above. The durations of the inspiratory and expiratory periods are respectively determined by the settings of variable restrictors 100 and 102. The ratios of inspiration to expiration duration may thus be varied to meet a diverse range of requirements.

For example, expiration time control 102 may be adjusted to provide inspirations with relatively long duration expiration, e.g. a ratio of inspiration to expiration of generally less than about one to five. This mode is considered an intermittent mandatory ventilation (IMV) which may be desirable to wean the patient away from dependence upon the respirator. IMV thus gradually (as the ratio is reduced) increases the patient's ability to sustain his own respirations.

The above description of the operation of the respirator 10 involved an inspiratory period during which the gas pressure at the patient port 18 was not sufficient to overcome the exhaust port 24 closing pressure exerted by diaphragm 28. This mode of operation is volume limited which results in the application of a constant volume of gas to the patient. However, when the maximum inspiration pressure control 94 is adjusted so that the gas pressure at the patient port 18 is sufficient to overcome the diaphragm closure force during each inspiratory period the respirator is operated in a pressure limited mode. When such upper pressure limit occurs, the excess gas at the patient connection 16 is dumped to atmosphere through exhaust port 24.

Another operating mode may be achieved with respirator 10 by closing valve 92 at the gas supply to effectively disable logic network 30. In such case only input port 82 of element 68 receives a supply of gas from source 88. In this mode the breathable gas mixture at the patient port 18 is allowed to be exhausted to atmosphere through port 24 in valve 22. However, the continuous presence of a back pressure from surce 88 as applied through restrictors 96, 98 and tube 64 to control chamber 26 assures a continuous positive airway pressure (CPAP) at the patient port 18. This mode is considered beneficial in treatment of diseases such as hyaline membrane disease.

When the gas supply source 88 as well as source 90 is removed by closing variable restrictor 96, the respirator is still functional and maintains a constant flow of gas past the patient port 18. This mode may, for example, be used to deliver a specified concentration of oxygen to a patient who does not require other respiratory support.

Having thus described a respirator in accordance with the invention, its many advantages can be appreciated. Gas is constantly flowed past the patient who thus may inspire at any time. The respirator may be formed with relatively inexpensive components and is sufficiently light in weight to render it portable. The variety of operating modes provide a versatile respirator suitable for treatment of many different disease states. The use of pneumatic controls provides a respirator which may be used in explosive environments.

What is claimed is:

[1. A compact respirator operating in an ambient environment comprising patient connection means having a patient port, an inlet port and a control port coupled in communication with the patient port for delivering breathable gas;

means for supplying the inlet port with a flow of breathable gas at a rate selected to aid the breathing cycle of a patient breathing gas from the patient port, said gas being continuously suppliable through the inlet port to the patient port and to the control port;

a control valve coupled between the control port and the ambient environment to controllably release gas from the control port for a corresponding control of gas at the patient port;

means including a pneumatically controlled bistable gas pressure controlling element operatively coupled to the control valve to control inspiratory gas flow to the patient port during one state of the bistable element and enable expiratory gas flow away from the patient port during the other state of the bistable element; and pneumatic oscillating means for providing cyclic gas pressures between levels selected to actuate the bistable gas pressure controlling element between its states, a first gas pressure level from the pneumatic oscillating means being selected to endure in correspondence with a desired length of time of inspiratory gas flow to the patient port and a second gas pressure level from the pneumatic oscillating means being selected to endure in correspondence with a desired length of time of the expiratory gas flow away from the patient port;

whereby the patient port may be provided with a continuous supply of breathable gas from the inlet port independent of the state of the control valve while producing inspiration and expiration respiratory support.]

[2. The respirator as claimed in claim 1 wherein the control valve is formed with an exhaust port and a diaphragm controllably interposed between the control port and the exhaust port to regulate the exhaust of gas from the patient through the control port to the exhaust port in response to gas pressure applied to one side of the diaphragm;

said one diaphragm side being coupled to the bistable gas pressure controlling element for diaphragm operational control thereby.]

[3. The respirator as claimed in claim 2 wherein said control valve is further provided with an emergency pressure release valve operatively coupled and selected to exhaust the breathable gas to ambient upon a predetermined maximum tolerable pressure level at the patient port.]

*4. A compact respirator operating in an ambient environment with a source of pressurized gas comprising*

*patient connection means having a patient port, an inlet port and a control port in communication with the patient port for delivering breathable gas;*

*means for supplying the inlet port with a flow of breathable gas at a rate selected to aid the breathing cycle from the patient port, said gas being continuously suppliable through the inlet port to the patient port and to the control port;*

*control valve means coupled between the control port and the ambient environment to controllably release gas from the control port for a corresponding control of gas at the patient port;*

*means including a pneumatically controlled bistable gas pressure controlling element operatively coupled to the control valve to control inspiratory gas flow to the patient port during one state of the bistable element and enable expiratory gas flow away from the patient port during the other state of the bistable element;*

[The respirator as claimed in claim 2 wherein the means to control inspiratory and expiratory gas flow at the patient port further includes]

[means producing a source of gas under pressure;]

[a] maximum pressure control *means* operatively coupled between the [gas] source [producing means] *of pressurized gas* and the bistable gas pressure controlling element to establish a desired maximum inspiratory pressure level [at the patient port; and] *on said control valve means and thereby regulate inspiratory gas flow to the patient port during one state of the bistable element effectively through the bistable gas pressure controlling element;*

[a] minimum pressure control *means* operatively coupled between the [gas] source [producing means] *of pressurized gas* and the bistable gas pressure controlling element to establish a desired expiratory pressure level [at the patient port] *on said control valve means and thereby regulate expiratory gas flow to the patient port during another state of the bistable element effectively through the bistable gas pressure controlling element; and*

*pneumatic oscillating means for providing cyclic gas pressures between levels selected to actuate the bistable gas pressure controlling element between its states, a first gas pressure level from the pneumatic oscillating means being selected to endure in correspondence with a desired length of time of inspiratory gas flow to the patient port and a second gas pressure level from the pneumatic oscillating means being selected to endure in correspondence with a desired length of time of the expiratory gas flow away from the patient port;*

*whereby the patient port may be provided with a continuous supply of breathable gas from the inlet port independent of the state of the control valve while producing inspiration and expiration respiratory support.*

5. The respirator as claimed in claim 4 [wherein said gas source producing means further includes] *and further including* means for interrupting the flow of gas from the source to the maximum pressure control while enabling gas flow to the minimum pressure control to provide a continuous pressure to the [diaphragm] *control valve* and establish a continuous positive airway pressure at the patient port.

6. The respirator as claimed in claim 4 wherein the pneumatic oscillating means further includes

*a pair of pneumatically operated bistable elements coupled in feed-back relationship to provide a pneumatic oscillator and a pneumatic delay element operatively interconnecting the pair of bistable elements to provide a time constant with the inspiration and expiration time control for control of the pneumatic oscillator;*

[an] inspiration time control *means* operatively responsive to the gas source [producing means] to provide an inspiration pressure control pulse [of] *through one of the pair of feed-back coupled bistable elements to the pneumatic delay element* a magnitude selected to establish the duration of the maximum inspiratory pressure level at the patient port; and

[an] expiration time control *means* operatively responsive to the gas source [producing means] to provide an expiratory pressure control pulse [of] *through said one bistable element in the pair of feed-back coupled bistable elements to the pneumatic delay element with* a magnitude selected to establish the duration of the desired expiratory pressure level.

[7. The respirator as claimed in claim 6 werein the pneumatic oscillating means further includes a pair of pneumatically operated bistable elements coupled in feed-back relationship to provide a pneumatic oscillator and a pneumatic delay element operatively interconnecting the pair of bistable elements to provide a time constant with the inspiration and expiration time control for control of the pneumatic oscillator.]

[8. The respirator as claimed in claim 7 wherein one of the pair of pneumatic bistable elements is coupled to drive the bistable gas pressure controlling element and the other of the pair of pneumatic bistable elements is coupled to the inspiration and expiration time controls.]

9. [A] *In a* respirator for supplying a patient with breathable gas from a supply of gas [comprising] *with*

[a.] a control valve having an input port, an exhaust port, a control chamber and means operatively located between the control chamber and the exhaust port to controllably release breathable gas to atmosphere at the exhaust port during inspiration and expiration cycles of the respirator;

[b.] tubing network means, having a patient port, for operatively coupling the supply of breathable gas to the input port of the control valve while enabling continuous breathing from the patient port;

[c. pneumatic control means operatively coupled to the control chamber for alternately pressurizing the control chamber to levels which respectively establish inspiratory and expiratory breathing conditions at the patient port in the tubing network means, said pneumatic control means including]

[i.] pressure control means for alternately producing high and low pressure levels in said valve control chamber with pressure levels being selected to determine the magnitude of the inspiratory and expiratory *pressure* conditions at the patient port,

[ii.] means for cycling the pressure control means between its high and low pressure levels at a rate and for respective durations selected to enable the varying pressures in the valve control chamber to establish desired inspiratory and expiratory *pressure* conditions at the patient port in the tubing network means,

[iii.] first variable means coupled to the cycling means for pneumatically controlling the cycling periods of the cycling means and establish correspondingly desired time periods for the inspiratory and expiratory conditions at the patient port, [and] *the improvement comprising*

[iv.] second variable means *effectively* coupled [to] *through* the pressure control means *to the control chamber in said control valve* for pneumatically selecting inspiratory and expiratory pressure levels in the control chamber of the control valve to correspondingly determine inspiratory and expiratory pressure levels of the gas supplied through the tubing network means to the patient.

[10. A respirator for supplying breathable gas from a supply of gas to a patient port comprising a. a control valve having an input port, an exhaust port and a control chamber and means for controllably releasing breathable gas to atmosphere from the exhaust port;

b. tubing network means having a patient port for coupling the supply of breathable gas to the input port of the control valve while enabling continuous breathing from the patient port;

c. pneumatic control means operatively coupled to the control chamber of the control valve for selectively pressurizing the control chamber to regulate the exhaust of breathable gas from the exhaust port and correspondingly and selectively establish inspiratory and expiratory breathing conditions at the patient port in the tubing network means, said pneumatic control means including i. variable pneumatic oscillator means for repetetively producing a pair of time variable pressure levels respectively corresponding to the time duration of the inspiratory and expiratory breathing conditions, and ii. means including a bistable pneumatic logic element coupled to said oscillating means to respond to the pair of time variable pressure levels produced in the variable pneumatic oscillator means and coupled to said supply of gas for generating a first gas pressure to the control chamber selected to enable an inspiratory state at the patient port with a first stable state of the logic element and a second gas pressure to the control chamber selected to enable an expiratory state at the patient port with a second stable state of the logic element.]

[11. The respirator as claimed in claim 10 wherein said means including the bistable pneumatic logic element further includes] *A respirator for supplying breathable gas from a supply of gas to a patient port comprising*

*a. a control valve having an input port, an exhaust port and a control chamber and means for controllably releasing breathable gas to atmosphere from the exhaust port;*

*b. tubing network means having a patient port for coupling the supply of breathable gas to the input port of the control valve while enabling continuous breathing from the patient port;*

*c. pneumatic control means operatively coupled to the control chamber of the control valve for selectively pressurizing the control chamber to regulate the exhaust of breathable gas from the exhaust port and correspondingly and selectively establish inspiratory and expiratory breathing pressure conditions at the patient port in the tubing network means, said pneumatic control means including*

*i. variable pneumatic oscillator means for repetetively producing a pair of time variable pressure levels respectively corresponding to the time duration of the inspiratory and expiratory breathing conditions,*

*ii.* a first variable restrictor selected to provide an output pressure [to correspond] *corresponding* with a desired maximum inspiration pressure[;] , [and]

*iii.* a second variable restrictor selectd to provide an output pressure [to correspond] *corresponding* with a desired minimum expiration pressure[;] , *and*

*iv. a bistable pneumatic logic element having a control port, input parts and an output port, with its control port effectively coupled to said oscillating means to respond to the pair of time variable pressure levels produced in the variable pneumatic oscillator means and with the input ports effectively coupled to said first and second variable restrictors to generate at the output port a first gas pressure effectively coupled to the control chamber and selected to enable an inspiratory pressure condition at the patient port with a first stable state of the logic element and to generate a second gas pressure to the control chamber selected to enable an expiratory pressure condition at the patient port with a second stable state of the logic element.*

12. The respirator as claimed in claim 11 wherein the pneumatic oscillator further includes a pair of bistable pneumatic logic elements, *each having a control port, input ports and an output port, with the output port of one element in the pair effectively* coupled in feedback relationship *to the control input of the other element in the pair,* one of said pair of logic elements [being] *having one input port* provided with a third variable restrictor [selected] to provide [an output pressure] *a gas flow rate* [whose] *through said one element with a* magnitude [is] selected to determine the time period desired for the inspiration cycle and a fourth variable restrictor [selected to provide] *effectively coupled to the other input port of said one element, said fourth variable restrictor* [an output pressure] *providing a flow rate through said one element with a*

[whose] magnitude [is] selected to determine the time period for the expiration cycle.

13. In a respirator for supplying a patient with *a* breathable gas from a supply of pressurized gas including patient communicating means for controlling the flow of breathable gas from said supply and from said patient communicating means to atmosphere, the improvement comprising first, second and third pneumatic elements each having an output port and a pair of input ports and a control port to select pneumatic communication between one input port and the output port;

*means for intercoupling said* first and second of said plurality of pneumatic elements being [intercoupled,] with the output port of each said latter elements being connected to the control port of said other of said first and second elements in positive feedback relationship to form a pneumatic oscillator, with the output port of the second pneumatic element providing a pneumatic output oscillating between pressure levels corresponding to the inspiratory and expiratory cycles for the respirator;

volume means coupled between the output port of said first pneumatic element and the control port of said second pneumatic element;

first variable means coupled between the supply of gas and one input port of the first pneumatic oscillator element and second variable means coupling the other input port of the first pneumatic element to atmosphere for respectively selecting the time periods for the inspiratory and expiratory cycles of the pneumatic oscillator;

a third pneumatic control element having its control port responsively communicating with the output port of the second pneumatic element in the pneumatic oscillator and having its output port connected to said means for controlling the flow of breathing gas; and third variable means coupled between the input ports of the third pneumatic control element and the supply of gas to select at the output port of the third pneumatic control element inspiratory and expiratory pressure levels for breathable gas supplied to the patient.

14. The respirator as claimed in claim 13 wherein the second variable means includes a variable expiratory duration determining gas flow restrictor effectively coupled between one input port of the first pneumatic oscillator element and ambient pressure, said first variable means further including a variable inspiratory duration determining gas flow restrictor effectively coupled between the other input port of the first pneumatic oscillator element and the supply of pressurized gas.

15. The respirator as claimed in claim 14 wherein the third variable means includes a variable expiratory pressure determining gas flow restrictor and a variable inspiratory pressure determining gas flow restrictor effectively coupled between said supply of pressurized gas and the respective input ports of the third control pneumatic element.

* * * * *